(12) United States Patent
Bacher

(10) Patent No.: US 6,299,625 B1
(45) Date of Patent: Oct. 9, 2001

(54) HANDLE FOR A MEDICAL INSTRUMENT

(75) Inventor: Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/545,377

(22) Filed: Apr. 7, 2000

Related U.S. Application Data

(63) Continuation of application No. PCT/EP99/05868, filed on Aug. 12, 1999.

(30) Foreign Application Priority Data

Aug. 12, 1998 (DE) ............................................. 198 36 481

(51) Int. Cl.$^7$ .................................................... A61B 17/28
(52) U.S. Cl. .......................... 606/170; 606/167; 606/205
(58) Field of Search ................................... 606/120, 142, 606/148, 167, 170, 205–206; 600/564; 7/133–135; 81/343–345; 294/2, 19.1, 23–24

(56) References Cited

U.S. PATENT DOCUMENTS

| 2,214,985 | 9/1940 | Bachmann . |
| 5,002,543 | 3/1991 | Bradshaw et al. . |
| 5,201,743 | * 4/1993 | Haber et al. ........................ 606/147 |
| 5,261,917 | 11/1993 | Hasson et al. . |
| 5,403,332 | 4/1995 | Christoudias . |
| 5,441,494 | * 8/1995 | Orti .................................... 606/205 |
| 5,456,684 | 10/1995 | Schmidt et al. . |
| 5,755,723 | * 5/1998 | Lombardo ........................... 606/170 |
| 6,017,358 | * 1/2000 | Yoon et al. ......................... 606/205 |
| 6,039,752 | * 3/2000 | Kimura .............................. 606/205 |

FOREIGN PATENT DOCUMENTS

| 198 36 481 C1 | 3/2000 | (DE) . |
| 0 640 319 A1 | 3/1995 | (EP) . |
| 0 705 569 A1 | 4/1996 | (EP) . |

* cited by examiner

Primary Examiner—Kennedy Schaetzle
Assistant Examiner—Kristen Droesch
(74) Attorney, Agent, or Firm—St. Onge Steward Johnston & Reens LLC

(57) ABSTRACT

A handle for a medical instrument which has two jaw parts movable independently of one another has a handle body on which two handle elements, movable independently of one another, for selectable actuation of the jaw parts are arranged. Arranged at the proximal end of the handle body is a thumb handle element which has a thumb ring. The movable handle elements are arranged in a manner spaced distally away from the thumb handle element on the handle body, and protrude laterally therefrom. The thumb handle element is rotatable about a longitudinal handle axis relative to the movable handle elements, so that the one and the other movable handle element are movable alternately into a position forming in each case with the thumb handle element a handle arrangement operable in scissor fashion.

18 Claims, 6 Drawing Sheets

HANDLE FOR A MEDICAL INSTRUMENT

CROSS-REFERENCE TO PENDING APPLICATION

This application is a continuation to pending International Application PCT/EP99/05868 filed Aug. 12, 1999.

BACKGROUND OF THE INVENTION

The present invention relates to a handle for a medical instrument which has two jaw parts movable independently of one another.

A handle of this kind is known from DE 694 3 583 T2, corresponding to EP 0 640 319 B1.

A handle as cited initially is provided for a medical instrument that has two jaw parts movable independently of one another. Forceps of this kind are used in endoscopic surgery, usually as multifunctional instruments, for example in order to cut tissue with the one jaw part and to grasp it with the other jaw part for removal of the tissue from the body. Accordingly, the one jaw part is configured as a cutting tool, whereas the other jaw part is shaped as a grasping tool. The two jaw parts are movable independently of one another, i.e. they can be closed and opened independently of one another. Both jaw parts can also possess a cutting function or a grasping function.

A handle of this kind for a medical instrument having two jaw parts movable independently of one another, and correspondingly two handle elements movable independently of one another, should be configured so that the physician can easily operate the handle without relearning the manner of operation of such an instrument, or needing to become accustomed to a new manner of operation.

With a predominant number of medical instruments, physicians are accustomed to a handle that is operable in scissor fashion, such as is known, for example, from DE-A-44 44 025 and sold by the company Karl Storz GmbH & Co., Tuttlingen, Germany, under the trademark "Takeapart." The advantage of these handles is that they can be held and operated with the thumb and the index and/or middle finger in the manner of a scissors. The two handle elements are configured such that they can be held with a hand position in which the back of the hand extends substantially vertically, which has the advantage that the wrist is then straight. Handles of this kind that are to be operated in scissor fashion have proven to be particularly ergonomic in the context of medical instruments, since it is possible to work in fatigue-free fashion with instruments having handles that are operated in scissor fashion.

The handles of scissor-like configuration described above have, however, hitherto been provided only for those medical instruments that have either only one movable jaw part or two jaw parts movable together. These known handles accordingly have only one movable handle element and one immovable handle element.

The aforementioned DE 694 03 533 T2 discloses a handle which that document refers to as a "manipulable surgical hand," which has three movable handle elements in order to allow tools at the distal end of a shaft to be actuated independently of one another. Of the three movable handle elements, one forms the thumb handle element and the other two form handle elements that are operable with the index and middle fingers. The handle elements actuable with the fingers are arranged distally from the thumb handle element, and laterally on the handle body. With this handle element arrangement, it is said that the natural movement capabilities of the human hand can be transferred in lifelike fashion to the tools at the distal end. This handle has at its proximal end a bracing plate against which the hand surface of the hand holding the handle rests; the handle is intended to constitute a "mechanical glove" into which the thumb and two fingers of the human operator can be inserted. This handle is accordingly always operated simultaneously with the thumb, index finger, and middle finger, one handle element on the handle body being allocated to each of these fingers. The handle elements are arranged, in this context, in the shape of a triangle. Leaving aside the fact that this handle is of very complex design because of its additionally provided functions, the configuration of this handle does not correspond to that of a scissor-handle arrangement. Instead, the thumb, index finger, and middle finger are spread apart in front of the hand when they engage into the respectively provided finger rings. Working with this handle requires long practice and particular dexterity.

In medical instruments having two jaw parts movable independently of one another, it is occasionally necessary to rotate the instrument as a whole about the instrument axis in order, for example after tissue has been detached with the one jaw part, to bring the other jaw part to the detached tissue in order then to grasp it with that jaw part. In this context, the entire instrument (including the handle) must be rotated as much as 180°, depending on the position of the jaw parts.

This is possible only with difficulty with the known handle cited above, since the thumb handle element does not permit rotation about the longitudinal axis of the handle.

A handle for a medical instrument having two jaw parts movable independently of one another and, correspondingly, two handle elements movable independently of one another is furthermore disclosed by U.S. Pat. No. 5,403,332. This handle is arranged in the shape of a T at the proximal end of the instrument shaft. The two movable handle elements protrude laterally from the instrument shaft, and are located distally in front of the proximal stationary handle. This handle is held in such a way that the rear transverse grip lies in the inner surface of the hand like a bar, so that the index and middle fingers and ring finger can fit around the movable handle elements configured as buttons, and can pull them proximally toward the transverse grip in order to actuate the jaw parts. This embodiment of a handle also does not correspond to that of a scissor-like handle arrangement.

A medical forceps having two jaw parts movable independently of one another and two handle elements movable independently of one another is also known from U.S. Pat. No. 2,214,985. A third handle element is arranged distally in front of and centeredly between the movable handle elements. The two movable handle elements and the immovable handle element each have a finger ring through which a finger or thumb can be inserted. The third, immovable handle element has a finger ring that is arranged in a plane perpendicular to the longitudinal axis of the forceps, this plane moreover running obliquely with respect to the planes of the two finger rings of the movable handle elements. This handle is held in such a way that the index finger is inserted through the distal immovable handle element, while the thumb and middle finger are inserted through two proximal laterally arranged finger rings. The result is that handle arrangement does not represent a handle arrangement that is operable in scissor fashion, as is known in medical instruments having only one movable jaw part or two jaw parts movable together, to which surgeons are accustomed.

It is therefore the object of the invention to develop a handle of the kind cited initially, for a medical instrument that has two jaw parts movable independently of one another, in such a way that the handle is ergonomic, that it becomes possible to work in fatigue-free fashion with the instrument, and that handling of the handle in order to actuate the two jaw parts is simplified.

SUMMARY OF THE INVENTION

According to the present invention a handle for a medical instrument which has a first jaw part and a second jaw part movable independently of one another, is provided comprising:

a handle body having a longitudinal handle axis, a movable first handle element and a movable second handle element arranged on said handle body, said first handle element and said second handle element being movable independently of one another, for selectable actuation of one of said first jaw part and said second jaw part, a thumb handle element arranged on said handle body at a proximal end thereof and having a thumb ring, said movable first and second handle elements being spaced distally away from said thumb handle element and protruding laterally from said handle body, wherein said thumb handle element is rotatable about said longitudinal handle axis so that said movable first and said second handle elements can be brought alternately into a position in which said first or, respectively, said second handle element form with said thumb handle element a handle arrangement which is operable in scissor fashion, and, in which position said thumb handle element and said first or, respectively, said second handle element lie substantially in a plane parallel to said longitudinal handle axis.

The handle according to the present invention is thus, in contrast to the known handle cited initially, configured as a double scissor-like handle arrangement, such that each of the movable handle elements can form a scissor-like arrangement with the one thumb handle element. This has the advantage that the handle can always be held in the manner of a scissors, regardless of whether the one movable handle element or the other is to be actuated in order to actuate the associated jaw part; this is familiar to the physician from handles for instruments having one movable jaw part or two jaw parts movable together, which have proven successful because of their ergonomics and which allow fatigue-free operation. The physician, who is already accustomed to a scissor-like handle on instruments having one movable jaw part, therefore does not need to switch over to a different handling style with an instrument having two jaw parts movable independently of one another. A "scissor-like handle arrangement" for the purposes of the invention is understood to mean that the thumb handle element and each of the movable handle elements can be held and actuated in the manner of a scissors; this does not, however, necessarily mean that the movable handle elements are pivotable. They can also be configured as linearly displaceable handle elements.

The common plane spanned by the thumb ring and the handle element forming with it the handle arrangement operable in scissor fashion preferably contains the longitudinal handle axis.

The lateral arrangement of the movable handle elements on the handle body contributes to improved ergonomics for the handle, since with a vertical position for the scissor handle arrangement constituted by the thumb handle element and one of the respective movable handle elements, the movable handle element lies below and in front of the thumb handle element, which corresponds to the anatomical positional relationship between the thumb and the index or middle finger when the back of the hand is held vertically.

Provision is also made according to the present invention for the thumb handle element, which has a thumb ring, to be rotatable. This yields the advantage that in order to rotate the instrument and then, after actuation of the one jaw part, to bring the other jaw part to the same location and then to actuate it, the thumb can remain inserted through the thumb ring. It is thus not necessary, in order to rotate the instrument, to release the handle completely and then grasp it again once the rotation operation is complete, thus achieving a further substantial simplification in the handling of the handle according to the present invention.

The handle according to the present invention is thus characterized by its excellent ergonomics and easy handling capability.

In a preferred embodiment, the two movable handle elements are arranged in circumferentially spaced-apart fashion, and form with the thumb ring substantially an equilateral triangle arrangement.

The advantage of this feature is that the two movable handle elements are spaced apart from one another on the handle body, so that one movable handle element is not in the way when the other handle element is being actuated. The spacing is maximal if the two movable handle elements are, as preferred, arranged diametrically opposite one another. The triangular arrangement also yields the advantage that the thumb ring and the two movable handle elements together form a symmetrical handle arrangement, so that the two movable handle elements form with the thumb handle element a substantially identical scissor-like handle arrangement, so that the manner of operation of the one movable handle element in conjunction with the thumb ring does not differ from the operation of the other movable handle element.

In a further preferred embodiment, the thumb ring and the two handle elements are together arranged in one plane.

The advantage here is that the two movable handle elements are thus maximally spaced apart circumferentially from one another (i.e. by 180°), so that the "inactive" handle element does not interfere with operation of the "active" handle element that is in working engagement with the jaw part currently being actuated.

In a further preferred embodiment, the thumb ring protrudes laterally from the handle axis in such a way that, with the handle element that together with it forms the scissor-like handle arrangement, it lies approximately at one height in terms of the spacing from the longitudinal handle axis.

This feature is particularly advantageous because it creates a respective handle arrangement in which, when the wrist is held straight, the thumb and the index and/or middle finger lie at the same height in accordance with their anatomical position, with no need for the thumb to be spread.

In a further preferred embodiment, the movable handle elements each have a finger ring, peripherally closed or open over part of the periphery, for insertion or placement of an index and/or middle finger.

This feature is advantageous if the two movable handle elements are not actuable against a spring force and thus do not automatically return to their initial position, this usually being provided in cutting and grasping forceps so that the physician does not need to work against a spring force in order to actuate the jaw parts and can thus better control the closing force required to close the jaw parts. In this case the finger rings provided for are advantageous in terms of the handling capability of the movable handle elements, since the finger rings can be pivoted distally and proximally without relocating the fingers. Configuring the finger ring to be open over part of the periphery, for example as a half-ring or three-quarter ring, has the further advantage that the finger in question can more easily be introduced into the ring.

In a further preferred embodiment, the thumb handle element is nonrotatably immobilized on the handle body in at least two working positions in which the thumb ring forms, with one of the movable handle elements in each case, the handle arrangement that is actuable in scissor-handle fashion.

This feature has the advantage, in terms of the rotatably configured thumb handle element, that the thumb handle element cannot be unintentionally rotated during actuation of the respective jaw part.

It is further preferred in this context if the thumb handle element automatically snap-locks to the handle element when the two rotational positions are reached.

It is advantageous in this context that the two working positions of the thumb handle element are well-defined; and that as a result of the automatic snap-locking of the thumb handle element on the handle body, no further manipulations (for example, actuation of a snap-locking button) are necessary in order to immobilize the thumb handle element nonrotatably.

In a further preferred embodiment, the thumb handle element is rotatable through a full circle in at least one rotation direction.

The advantage of this feature is that the handle body with the movable handle elements arranged thereon can always be rotated in the same rotation direction in order to move the thumb handle element, alternately with the one or the other movable handle element, into the position forming the scissor-like handle arrangement. It is also preferred if the thumb handle element is rotatable through a full circle in both rotation directions.

In a further preferred embodiment, the thumb handle element is mounted on the handle body in axially movable fashion relative thereto, wherein the thumb handle element can be pulled axially in the proximal direction back from the handle body into a rotational position, in which it is rotatable.

The advantage of this feature is that the physician can pull the thumb handle element with the thumb inserted through the thumb ring, in the proximal direction out of the nonrotatable working position, as a result of which the thumb handle element can be moved into its rotational position by easy manipulation. This is advantageous especially in conjunction with the automatic snap-locking of the thumb handle element when the respective working position is reached, since the thumb handle element can then automatically snap into the nonrotatable working position by releasing the pulling force on the thumb ring.

It is further preferred in this context if the thumb handle element and the handle body are nonrotatably immobilized by way of an axially separable pin-and-hole connection.

This feature creates, in a simple manner that is advantageous in terms of design, a rotation prevention system for the thumb handle element in the working positions, which moreover makes possible easy unlocking by moving the thumb handle element axially.

In a further preferred embodiment, the thumb handle element is pre-loaded in the distal direction by way of a compression spring acting between it and the handle body.

This feature creates, in conjunction with the aforementioned pin-and-blind-hole connection, a snap-lock mechanism that is of advantageously simple design, which makes possible automatic snap-locking of the thumb handle element on the handle body, and which moreover is easy to release for rotation of the thumb handle element.

In a further preferred embodiment, the movable handle elements are arranged pivotably on the handle body.

This is advantageous because pivotably mounted handle elements can be configured as two-armed levers with a high capacity for energy transfer.

In a further preferred embodiment, immobilization means are provided which, when the thumb handle element is in a working position in which the thumb handle element forms the handle arrangement operable in scissor fashion with the one movable handle element, immobilizes the jaw part joined to the other movable handle element in its closed position, and vice versa.

The particular advantage of this feature is that the "inactive" jaw part, which does not need currently to be moved for a procedure in the body, is held in positionally fixed fashion in its closed position, and cannot unintentionally or inadvertently open and thereby represent an impediment.

It is further preferred in this context if the movable handle elements are each in working engagement with the associated jaw part via an axially movable control rod, and the immobilization means immobilize the respective control rod in a position in which the associated jaw part is closed.

It is advantageous in this context that immobilizing or locking the "inactive" jaw part by immobilizing the control rod makes possible particularly effective immobilization, which engages directly on the control rod itself.

In a further preferred embodiment, the immobilization means have a rotatable sleeve that is arranged at the distal end of the thumb handle element and that has on one inner circumferential segment an inwardly projecting protrusion that, in order to immobilize the respective control rod that is to be immobilized, engages into a recess in that control rod.

This feature creates an immobilization capability of particularly simple design for the particular jaw part that is not involved, which advantageously is easy to integrate into the thumb handle element and, in conjunction with the rotatability thereof, allows easy operation.

It is further preferred if the protrusion comes into engagement with the recess by rotation of the thumb handle element into the desired working position.

In conjunction with the rotatable configuration of the thumb handle element, this embodiment is advantageous in particular in terms of especially easy handling, since immobilization of the "inactive" (i.e. non-participating) jaw part occurs more or less automatically when the thumb handle element is rotated about the longitudinal handle axis in order to form, with the other handle element, the handle arrangement operable in scissor-handle fashion.

The aforementioned advantages of the handle according to the present invention are used in a medical instrument that has two jaw parts movable independently of one another.

It is further preferred in the context of the medical instrument if the closing direction of the respective jaw part and the movement direction of the corresponding movable handle element in terms of the thumb handle element lie in approximately the same plane.

Handling of the instrument is further simplified if the two jaw parts are arranged, in terms of the handle arrangement constituted by the respective movable handle element and the thumb handle element, in such a way that the closing direction of the respective jaw part and the movement direction of the corresponding movable handle element lie in approximately the same plane in terms of the thumb handle element. The medical instrument having two jaw parts movable independently of one another that is equipped with the handle according to the present invention can thus be operated, in terms of both jaw parts, like a conventional instrument that has only one movable jaw part and has a scissor-like handle.

All in all, the invention makes it possible to combine two conventional complete instruments having one movable jaw part and one handle into an instrument that has two jaw parts movable independently of one another and has only one handle, with no degradation in the ergonomics of the handle of the combined instrument as compared to the handles of the conventional single instrument.

Further advantages are evident from the description below and the appended drawings.

It is understood that the features mentioned above and those yet to be explained below can be used not only in their respective combination indicated, but also in other combinations or in isolation, without leaving the context of the present invention.

BRIEF DESCRIPTION OF THE DRAWINGS

An exemplary embodiment of the invention is shown in the drawings and will be explained hereinafter in more detail with reference to the Figures, in which.

DETAILED DESCRIPTION OF PREFERRED EMBODIMENTS

Figure 1:
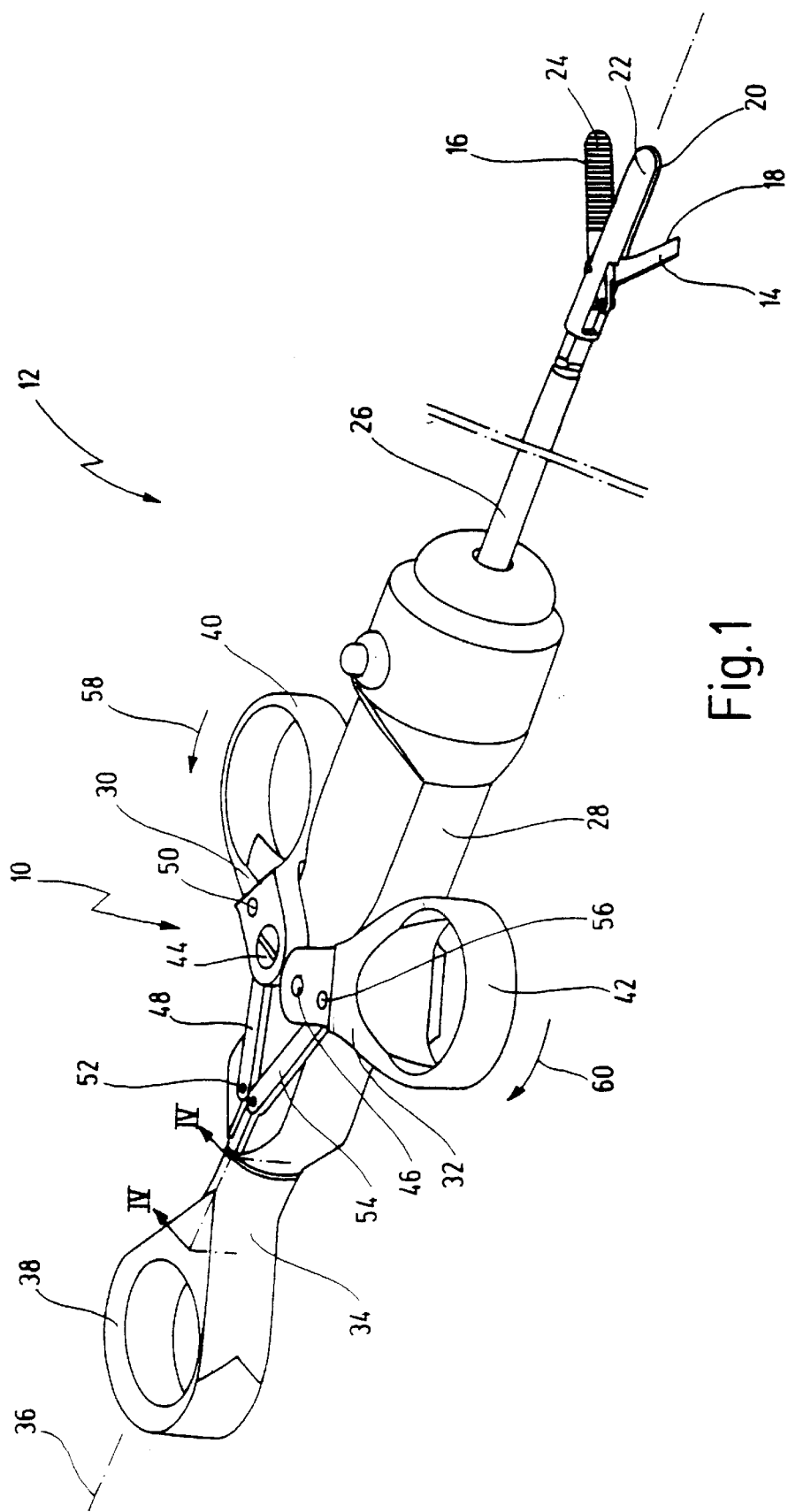
FIG. 1 shows a medical instrument, equipped with the handle according to the present invention, having two jaw parts movable independently of one another.

FIG. 1 shows a handle labeled with the general reference character 10, for a medical instrument labeled with the general reference character 12.

Medical instrument 12 has at its distal end a first movable jaw part 14 and a second movable jaw part 16. First jaw part 14 and second jaw part 16 are movable independently of one another, i.e. they can be opened and closed independently of one another.

In the exemplary embodiment shown, first jaw part 14 has a cutting function and is configured for that purpose with a cutting edge 18 which, as jaw part 14 closes, coacts in cutting fashion with a cutting edge 20 of an immovable base jaw part 22. With first jaw part 14, it is thus possible to detach tissue in cutting fashion in the human or animal body.

Second jaw part 16 is configured as a grasping tool, and for that purpose has a toothed surface 24 that coacts with a correspondingly toothed surface (not visible in FIG. 1) configured on base jaw part 22 in order to grasp tissue.

In an endoscopic surgical procedure, instrument 12 is thus used to cut tissue and to grasp the cut-off tissue in order to remove the detached tissue from the body. It is understood, however, that other jaw parts with other functions can also be used in the context of the invention.

Handle 10 is arranged at the proximal end, i.e. remote from the jaw parts, of instrument 12; a shaft 26 extends from handle 10 approximately to jaw parts 14 and 16.

Handle 10 has a handle body 28 in the form of a housing. A first movable handle element 30 and a second movable handle element 32 are arranged on handle body 28.

Arranged at the proximal end of handle body 28 is a thumb handle element 34 which, as will be described in further detail, is rotatable.

First movable handle element 30 and second movable handle element 32 are arranged distally from thumb handle element 34, and protrude laterally from handle body 28.

First movable handle element 30 and second movable handle element 32 are arranged on handle body 28 opposite one another and symmetrically with respect to one another in terms of a longitudinal handle axis 36 that forms the longitudinal center axis of handle 10 and also of the entire instrument 12.

Figure 2:
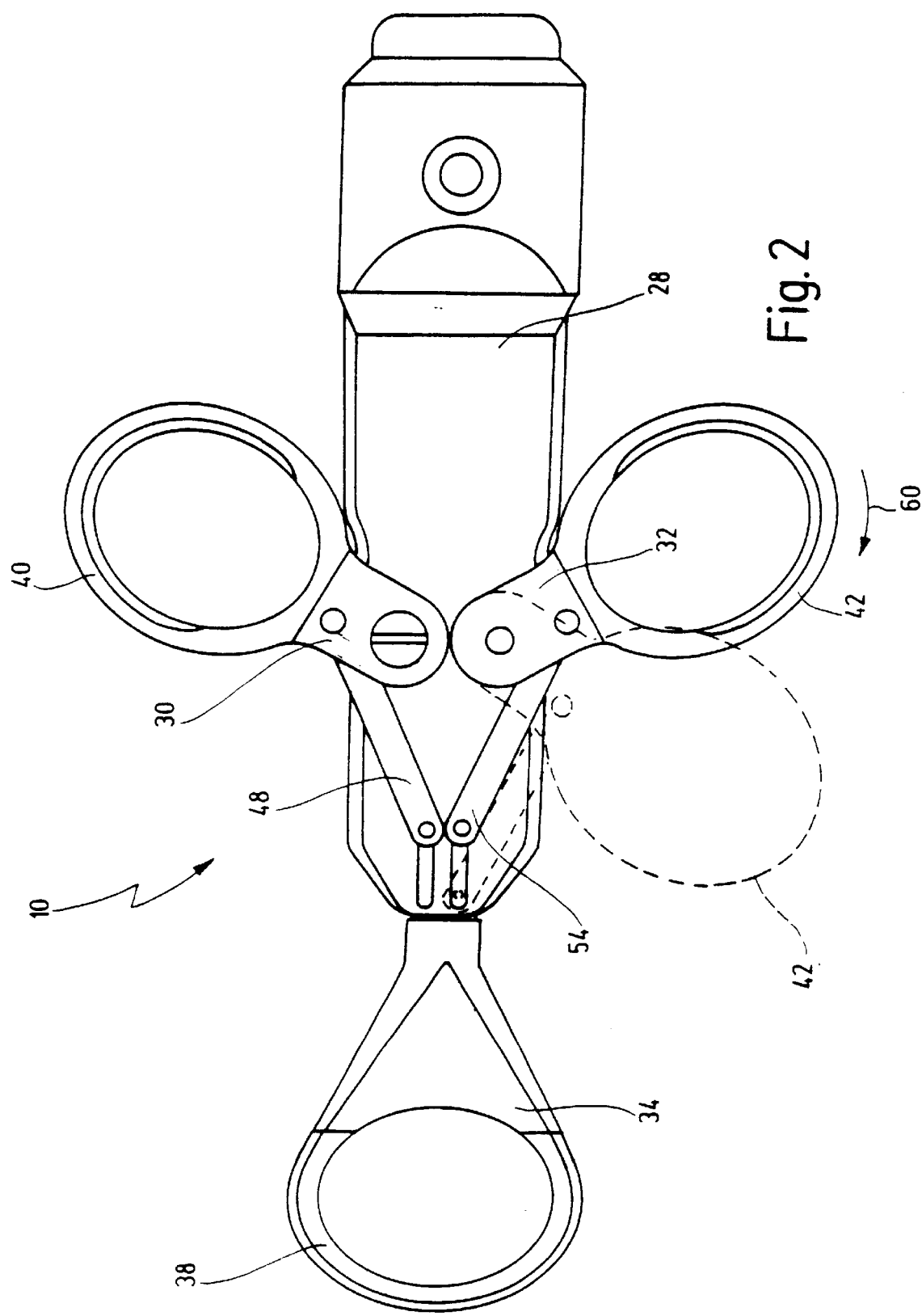
FIG. 2 shows a side view of the handle of FIG. 1 in isolation, showing the position of the handle during use.

Thumb handle element 34 and movable handle elements 30 and 32 lie substantially in one common plane, and in their positions as shown in FIGS. 1 and 2 span an approximately equilateral triangle.

Thumb handle element 34 has a thumb ring 38 through which the thumb of one hand can be inserted, while first movable handle element 30 has a finger ring 40, and second movable handle element 32 a finger ring 42, through which a finger of the same hand can be inserted, as will be described in more detail hereinafter with reference to the description of the handling of handle 10.

First movable handle element 30 serves to actuate the opening and closing of first jaw part 14, while second movable handle element 32 serves to actuate the opening and closing of second jaw part 16. First handle element 30 and second handle element 32 are mounted on handle body 28 so as to move independently of one another.

For that purpose, first movable handle element 30 is attached to handle body 28 via a hinge joint 44, and second movable handle element 32 via a hinge joint 46, pivotably about the respective hinge axis.

Energy transfer from first movable handle element 30 to first movable jaw part 14 is accomplished via an actuation mechanism that has a lever linkage 48. This is pivot-mounted at its distal end on movable handle element 30 at a pivot point 50 that is spaced away from hinge joint 44. At its proximal end 52, the lever linkage is joined to a first control rod, extending through handle body 28 and shaft 26 to first movable jaw part 14 and is not visible in FIG. 1, which is nonpositively connected to the latter.

In similar fashion, second movable handle element 32 is nonpositively connected, via a lever linkage 54 whose distal end is pivot-mounted at a pivot point 56 on movable handle element 32, and via a second control rod joined to lever linkage 54 and also not shown, to second movable jaw part 16.

In FIG. 1, first movable handle element 30 and second movable handle element 32 are shown in their respective maximally distal pivot positions, in which first jaw part 14 and second jaw part 16 assume their maximally open positions. If first movable handle element 30, for example, is then pivoted in the direction of an arrow 58 toward the proximal end, first movable jaw part 14 is closed. To open first movable jaw part 14 from the closed position, first movable handle element 30 is pivoted opposite to arrow 58.

Independently of first movable handle element 30, second movable handle element 32 can be pivoted toward the proximal end as shown by an arrow 60, thus closing second movable jaw part 16 which in the reverse direction is opened again.

In order for instrument 12 to be used in a procedure, handle 10 is held in a position as shown in FIG. 2. With handle 10 in this position, the scissor-handle arrangement constituted by movable handle element 32 and thumb handle element 34 stands approximately vertically.

With handle 10 in this position, instrument 12 can be held with the wrist straight, by inserting the thumb of one hand through thumb ring 38 and a finger of the same hand—for example the index or middle finger or both—through finger ring 42 of second movable handle element 32. With handle 10 in the position shown in FIG. 2, finger ring 42 of second movable handle element 32 is arranged below thumb ring 38, which corresponds to the anatomical positional relationship between thumb and index finger when the hand is held with the back of the hand extending approximately vertically.

Using the finger inserted through finger ring 42 and the thumb inserted through thumb ring 38, second movable handle element 32 can now be actuated, in the manner of a scissors, to close and open second movable jaw part 16.

Because of the symmetrical arrangement of movable handle elements 30 and 32, handle 10 can now be rotated 180° about longitudinal handle axis 36 so that first movable handle element 30 then lies in vertical terms below thumb handle element 34, while second movable handle element 32 then ends up above thumb handle element 34. After a 180° rotation of handle 10, thumb handle element 34 and first movable handle element 30 then form an arrangement operable in scissor fashion, so that first jaw part 14 can then also be actuated in the manner of a scissors using the same hand position as described earlier for second movable jaw part 16.

It is not necessary, however, to rotate the entire handle 10 in order to move first handle element 30 with thumb handle element 34 from the position shown in FIG. 2 into a position forming a handle arrangement operable in scissor fashion, since thumb handle element 34 is rotatable on handle body 28 about longitudinal handle axis 36.

For that purpose, thumb handle element 34 has a sleeve-like extension 62 (cf. FIG. 4) that overlaps a cylindrical end segment 64 of handle body 28. Sleeve-like extension 62 is displaceable axially, in the direction of an arrow 66, on cylindrical end segment 64; a compression spring 68, which is attached on the one hand to thumb handle element 34 and on the other hand to handle body 28, forces thumb handle element 34 in the distal direction opposite to arrow 66.

Also attached noncenteredly on cylindrical end segment 64 of handle body 28 is a pin 70 which projects out of the proximal end of segment 64 and engages into a blind hole or hole 72 recessed into thumb handle element 34. Diametrically opposite hole 72, a further corresponding hole (not shown) is provided in thumb handle element 34. When pin 70 engages into hole 72 or the correspondingly provided second hole, thumb handle element 34 is nonrotatably immobilized on handle body 28. Thumb handle element 34 thus has two working positions, in terms of movable handle elements 30 and 32, in which it is nonrotatable with respect to said movable handle elements 30 and 32. In these working positions, thumb handle element 34 and movable handle element 30 or movable handle element 32 respectively form the scissor-handle arrangement.

Figure 3:
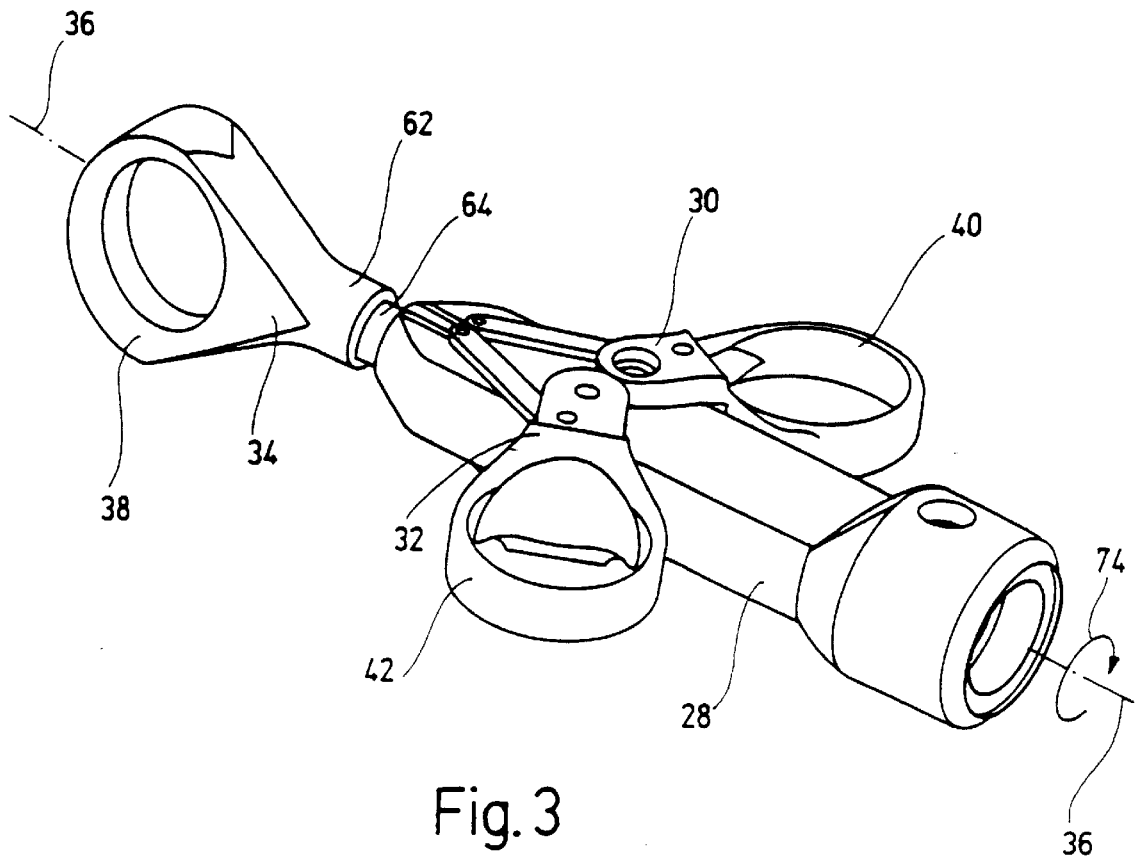
FIG. 3 shows the handle of FIG. 2 in a perspective representation, which illustrates the rotatability of the two movable handle elements relative to the thumb handle element of the handle.
Figure 4:
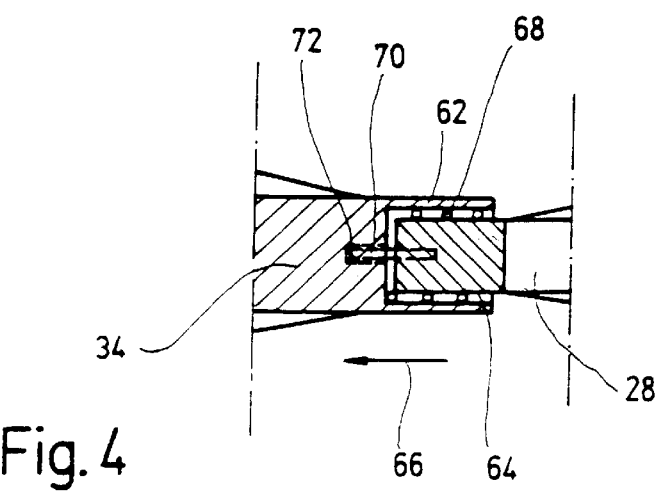
FIG. 4 shows a longitudinal section along line IV—IV in FIG. 1 through a portion of the handle of FIG. 1.

In order to unlock thumb handle element 34 from the working position shown in FIG. 2, the thumb inserted through thumb ring 38 is used to pull thumb handle element 34 proximally in the direction of arrow 66 as shown in FIG. 4 until pin 70 has emerged from hole 72. Thumb handle element 34 can now be rotated on handle body 28, as shown in FIG. 3. The instrument does not need to be removed for that purpose from the human or animal body, but can remain in situ. While thumb ring 38 is held in place with the thumb inserted through it, handle body 28 is rotated approximately 180° about longitudinal handle axis 36 as shown by an arrow 74, thus also causing the two jaw parts 14 and 16 to be co-rotated about longitudinal handle axis 36. Thumb ring 38 does not need to be kept pulled back during the rotation, since pin 70 of end segment 64 can now brace against the proximal wall of sleeve-like extension 62 and thereby keep the thumb handle element pulled back. As soon as the rotational position offset by 180° has been reached, pin 70 automatically engages, under the action of compression spring 68, into the hole arranged diametrically opposite hole 72, so that thumb handle element 34 is once again nonrotatably snap-locked on handle body 28. The same finger that was previously used to actuate second movable handle element 32 can now be inserted through finger ring 40 of first movable handle element 30 in order to actuate first movable handle element 30 and thus first movable jaw part 14.

If it is desired that then second jaw part 16 once again be actuated, the operation described above of rotating the movable handle elements 30 and 32 relative to thumb handle element 34 can be repeated; the rotation can always be accomplished in the same rotational direction with respect to thumb handle element 34, since thumb handle element 34 is mounted on handle body 28 so as to rotate through a full circle.

Jaw parts 14 and 16 are arranged, in terms of movable handle elements 30 and 32 and thumb handle element 34, in such a way that the closing direction of jaw part 16 and the movement direction of movable handle element 32 with respect to thumb handle element 34 lie in approximately the same plane. A corresponding situation exists for movable jaw part 14. As is further evident from FIG. 1, first movable jaw part 14 and the associated movable handle element 30, and movable jaw part 16 and the associated movable handle element 32, are arranged oppositely in terms of longitudinal handle axis 36.

Figure 5:
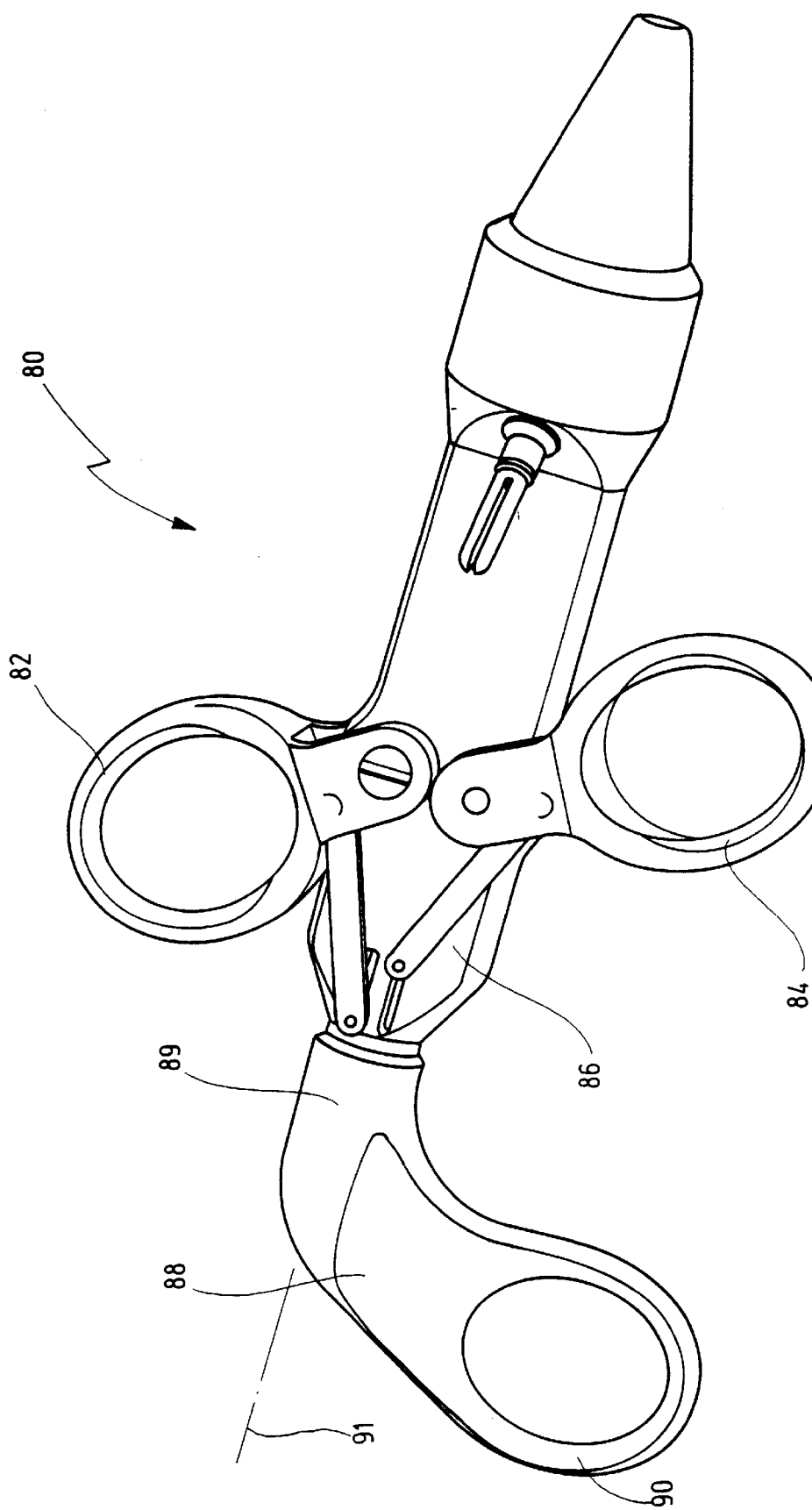
FIG. 5 shows a further exemplary embodiment of a handle according to the present invention, in an overall perspective representation.
Figure 6:
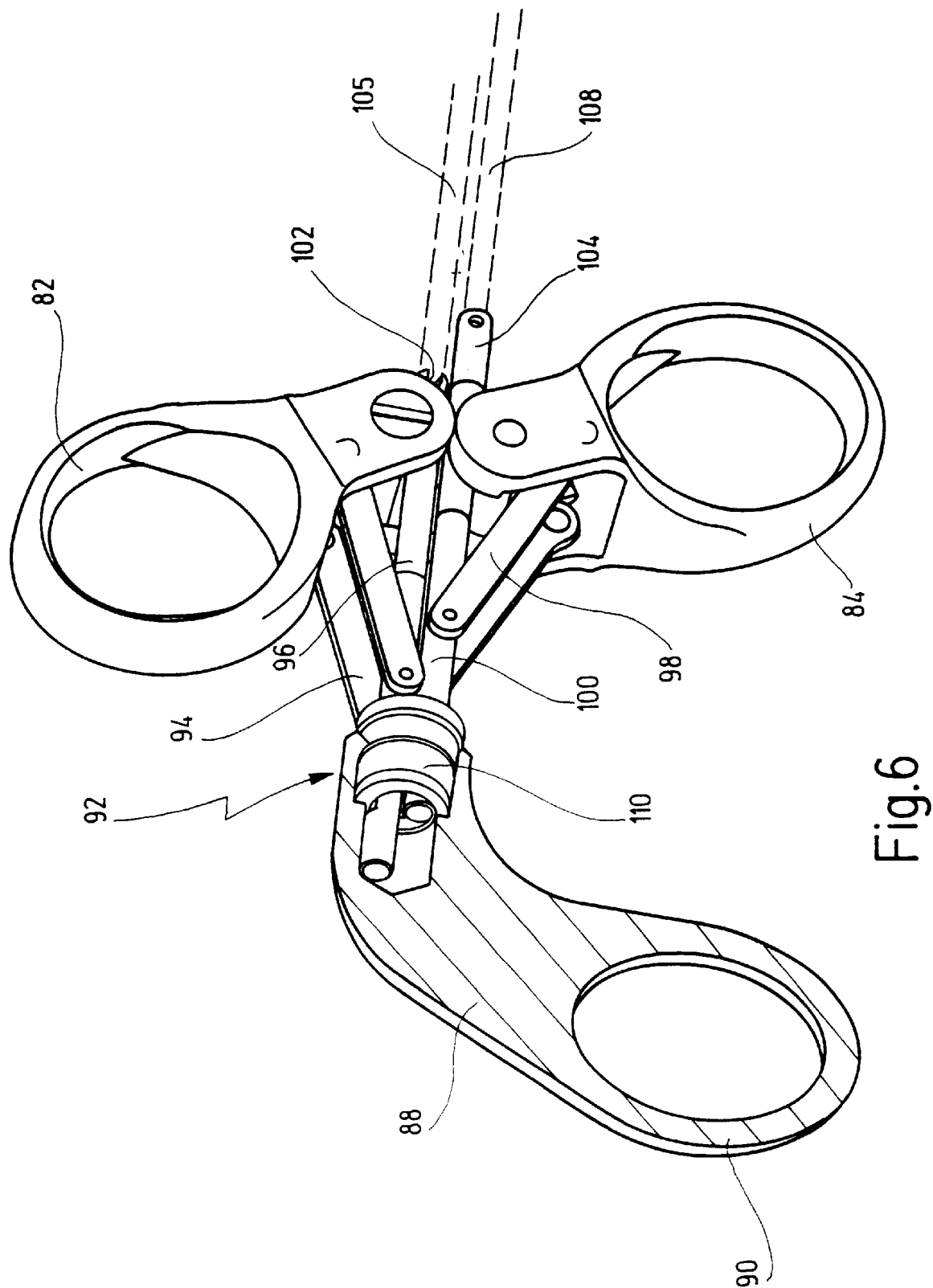
FIG. 6 shows a portion of the handle of FIG. 5, the handle housing having been omitted.
Figure 7:
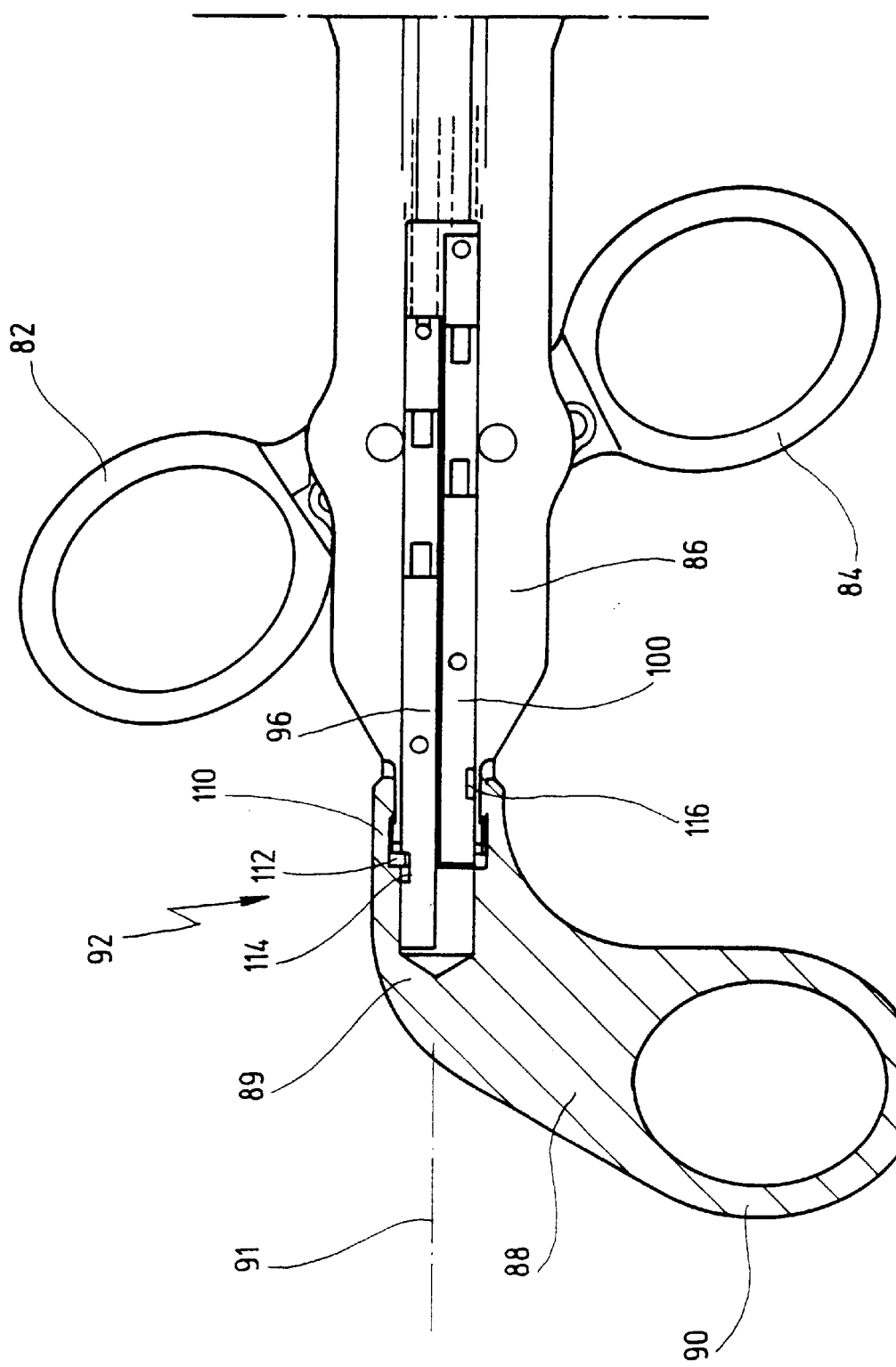
FIG. 7 shows a side view of the handle of FIGS. 5 and 6 in a schematic cutaway representation.

FIGS. 5 through 7 show a further exemplary embodiment of a handle labeled with the general reference character 80, whose differences from handle 10 as shown in FIGS. 1 through 4 will be described below. Features of handle 80 that are not described are identical or comparable to the corresponding features of handle 10.

Handle 80 can be used, for example, instead of handle 10 on medical instrument 10 shown in FIG. 1.

Handle 80 has a first movable handle element 82 and a second movable handle element 84; first movable handle element 82 and second movable handle element 84 are once again movable independently of one another, for example in order to move jaw parts 14 and 16 at the distal end of medical instrument 12 independently of one another.

A thumb handle element 88 is arranged at the proximal end of a handle body 86. Thumb handle element 88 has a thumb ring 90.

Thumb handle element 88 is rotatable about a longitudinal handle axis 91 of handle body 86, specifically through at least 180° in both rotation directions.

Thumb handle element 88 is attached at its attachment segment 89 to handle body 86 concentrically with longitudinal handle axis 91; thumb ring 90 protrudes laterally from longitudinal handle axis 91.

In the working position shown in FIGS. 5 through 7, thumb handle element 88 forms with movable handle element 84 a handle arrangement operable in scissor fashion.

By rotating thumb handle element 88 180° about longitudinal handle axis 91, thumb handle element 88 then forms with movable handle element 82 a handle arrangement operable in scissor fashion.

As is evident from FIGS. 5 through 7, thumb ring 90 together with movable handle element 84 (or more precisely its finger ring) lies at approximately the same height in terms of the spacing from longitudinal handle axis 91, thus creating a particularly ergonomic hand position and operation of movable handle element 84 for actuating the associated jaw part (not shown) at the distal end of the instrument. By rotating thumb handle element 88 180° about longitudinal handle axis 91, the same ergonomically favorable arrangement is created with the other movable handle element 82.

Referring to FIGS. 6 and 7, a description will now be given of immobilization means 92, with which selectably either first movable handle element 82 or second movable handle element 84 can be immobilized.

First movable handle element 82 is nonpositively connected via a linkage 94 to a first control rod 96 in order to be able to open and close the associated jaw part at the distal end of the instrument, as is also provided in the case of handle 10 as shown in FIGS. 1 through 4.

Second movable handle element 84 is correspondingly nonpositively connected, via a linkage 98, to a second control rod 100 in order correspondingly to open or close the other jaw part. Control rods 96 and 100 are axially movable independently of one another for this purpose.

First control rod 96 and second control rod 100 have respective mounting systems 102 and 104, so that control rod segments 106 and 108 (indicated with dashed lines) joined to the jaw parts can be detached from handle 80.

Thumb handle element 88 has a sleeve 110 into which control rods 96 and 100 engage.

As shown in FIG. 7, sleeve 110 has on an inner circumferential segment an inwardly projecting protrusion 112.

Control rod 96 has at its proximal end a recess 114, while control rod 100 also has a recess 116 which is arranged diametrically opposite recess 114 of control rod 96. Control rods 96 and 100 are arranged nonrotatably in handle body 86.

In FIGS. 6 and 7, control rod 96 is pulled back into its axially maximally proximal position, in which first movable handle element 82 is also pivoted back in the proximal direction.

With movable handle element 82, and control rod 96, in this position, the associated jaw part at the distal end of the instrument is in its closed position.

In this position, protrusion 112 in sleeve 110 of thumb handle element 88 engages into recess 114 of control rod 96, so that control rod 96 and thus movable handle element 82 are immobilized. The associated jaw part is thus also immobilized in its closed position.

Second movable handle element 84, which, when thumb handle element 88 is in this rotational position, forms therewith the handle arrangement operable in scissor fashion, is free to pivot, however, so that the jaw part that is in working engagement with this movable handle element 84 can be opened and closed by actuating handle element 84.

When thumb handle element 88 is rotated 180° about longitudinal handle axis 92, protrusion 112 releases from recess 114 in control rod 96 and then comes into engagement with recess 116 of control rod 100, so that control rod 100 and thus movable handle element 84 and the associated jaw part are immobilized in the closed position. For that purpose, movable handle element 84 is first pivoted in the direction toward the proximal end in order to bring control rod 100 into the maximally proximal position, so that protrusion 112 can engage into recess 116.

The configuration of immobilization means 92 thus always guarantees that the movable handle element which does not form, with thumb handle element 88, the handle arrangement actuable in scissor fashion, is immobilized or inactivated.

Thumb handle element 88 is also rotationally immobilized in both working positions.

What I claim is:

1. A handle for a medical instrument which has a first jaw part and a second jaw part movable independently of one another, said handle comprising:

a handle body having a longitudinal axis, a movable first handle element and a movable second handle element arranged in a plane on said handle body, said first handle element and said second handle element being movable independently of one another, for selectable actuation of one of said first jaw part and said second jaw part, and having first and second finger holders centered on parallel finger holder axes perpendicular to said plane, a thumb handle element arranged on said handle body at a proximal end thereof and having a thumb ring which is centered on a thumb ring axis, said movable first and second handle elements being spaced distally away from said thumb handle element and protruding laterally away from said handle body, wherein said thumb handle element is rotatable about said longitudinal axis so that said movable first and second handle elements can be brought alternatively into a position in which said first or, respectively, said second handle element form with said thumb handle element a handle arrangement which is operable in scissor fashion, wherein said thumb ring axis and either of the finger holder axes extend parallel to one and another and perpendicular to said plane, and, in which position said thumb handle element and said first or, respectively, said second handle element lie substantially in a common plane.

2. The handle of claim 1, wherein said movable first and second handle elements are arrange in circumferentially spaced-apart fashion, and form with said thumb ring substantially an equilateral triangle.

3. The handle of claim 1, wherein said thumb ring and said movable first and second handle elements are together arranged in one plane.

4. The handle of claim 1, wherein said thumb ring protrudes laterally from said handle axis in such a way that, said thumb ring is spaced from said longitudinal handle axis by approximately the same distance as the one of said first and second handle elements that together with t forms said scissor-like handle arrangement.

5. The handle of claim 1, wherein said movable first and second handle elements each have a finger ring, peripherally closed or open over part of the periphery, for insertion or placement of at least one of an index and a middle finger.

6. The handle of claim 1, wherein said thumb handle element is nonrotatably immobilized on said handle body in at least two working positions in which said thumb handle element forms, with one of said movable first and second handle elements in each case, said handle arrangement that is actuable in scissor-handle fashion.

7. The handle of claim 6, wherein said thumb handle element automatically snap-locks to said handle element when said two rotational positions are reached.

8. The handle of claim 1, wherein said thumb handle element is rotatable though a full circle in at least one rotation direction.

9. The handle of claim 1, wherein said thumb handle element is mounted on said handle body in axially movable fashion relative thereto, wherein said thumb handle element can be pulled axially in the proximal direction back from said handle body into a rotational position, in which it is rotatable.

10. The handle of claim 9, wherein said thumb handle element and said handle body are nonrotatably immobilized by way of an axially separable pin-and-hole connection.

11. The handle of claim 1, wherein said thumb handle element is mounted on said handle body in axially movable fashion relative thereto, wherein said thumb handle element can be pulled axially in the proximal direction back from said handle body into a rotation position, in which it is rotatable, and wherein said thumb handle element is preloaded in the distal direction by way of a compression spring acting between it and said handle body.

12. The handle of claim 1, wherein said movable first and second handle elements are arranged pivotably on said handle body.

13. The handle of claim 1, wherein immobilization means are provided which, when said thumb handle element is in a working position in which said thumb handle element forms said handle arrangement operable in scissor fashion with one of said movable first and second handle elements, immobilizes the one of said first and second jaw parts joined to the other of said movable first and second handle elements in its closed position, and vice versa.

14. The handle of claim 13, wherein said movable first and second handle elements are each in working engagement with said associated one of the said movable first and second jaw parts via an axially movable control rod, and wherein said immobilization means immobilize said respective control rod in a position in which the associated one of said first and second jaw part is closed.

15. The handle of claim 14, wherein said immobilization means have a rotatable sleeve that is arranged at a distal end of said thumb handle element and that has on one inner circumferential segment an inwardly projecting protrusion that, in order to immobilize said respective control rod that is to be immobilized, engages into a recess in that control rod.

16. The handle of claim 15, wherein said protrusion comes into engagement with said recess by rotation of said thumb handle element into the desired working position.

17. A medical instrument comprising a first jaw part and a second jaw part movable independently of one another, and comprising a handle, said handle comprising:

a handle body having a longitudinal axis, a movable first handle element and a movable second handle element arranged in a plane on said handle body, said first handle element and said second handle element being movable independently of one another, for selectable actuation of one of said first jaw part and said second jaw part, and having first and second finger holders centered on parallel finger holder axes perpendicular to said plane, a thumb handle element arranged on said handle body at a proximal end thereof and having a thumb ring which is centered on a thumb ring axis, said movable first and second handle elements being spaced distally away from said thumb handle element and protruding laterally away from said handle body, wherein said thumb handle element is rotatable about said longitudinal axis so that said movable first and second handle elements can be brought alternatively into a position in which said first or, respectively, said second handle element form with said thumb handle element a handle arrangement which is operable in scissor fashion, wherein said thumb ring axis and either of the finger holder axes extend parallel to one and another and perpendicular to said plane, and, in which position said thumb handle element and said first or, respectively, said second handle element lie substantially in a common plane.

18. The medical instrument of claim 17, wherein a closing direction of said respective jaw part and a movement direction of the corresponding one of said movable first and second handle elements lie in approximately the same plane with respect to said thumb handle element.

* * * * *